(12) United States Patent
Kratz

(10) Patent No.: US 7,445,764 B1
(45) Date of Patent: Nov. 4, 2008

(54) CARRIER-DRUG CONJUGATE

(75) Inventor: Felix Kratz, Ihringen (DE)

(73) Assignee: KTB Tumorforschungsgesellschaft mbH, Freiburg Im Breisgau (DE)

( * ) Notice: Subject to any disclaimer, the term of this patent is extended or adjusted under 35 U.S.C. 154(b) by 658 days.

(21) Appl. No.: 10/009,854

(22) PCT Filed: Jun. 7, 2000

(86) PCT No.: PCT/EP00/05254

§ 371 (c)(1), (2), (4) Date: Mar. 7, 2002

(87) PCT Pub. No.: WO00/76550

PCT Pub. Date: Dec. 21, 2000

(30) Foreign Application Priority Data

Jun. 10, 1999 (DE) ................. 199 26 475

(51) Int. Cl.
- *A61K 38/38* (2006.01)
- *A61K 47/48* (2006.01)
- *A61K 49/00* (2006.01)
- *A61K 49/14* (2006.01)
- *A61K 51/08* (2006.01)

(52) U.S. Cl. ............... 424/1.69; 424/9.1; 424/9.34; 424/9.6; 424/85.1; 424/649; 514/2; 514/8; 514/21; 514/34; 530/363; 530/408; 530/409; 530/410; 536/6.4

(58) Field of Classification Search .............. None
See application file for complete search history.

(56) References Cited

U.S. PATENT DOCUMENTS

| | | | |
|---|---|---|---|
| 6,124,255 A * | 9/2000 | Schlag et al. ............... | 514/2 |
| 6,310,039 B1 * | 10/2001 | Kratz ............................ | 514/8 |
| 6,706,892 B1 * | 3/2004 | Ezrin et al. ................. | 548/548 |
| 7,090,851 B1 * | 8/2006 | Bridon et al. ............ | 424/194.1 |
| 7,105,160 B1 * | 9/2006 | Smith ........................ | 424/179.1 |

FOREIGN PATENT DOCUMENTS

| | | |
|---|---|---|
| DE | 196 36 889 A | 3/1998 |
| WO | 93/08842 | 5/1993 |
| WO | WO 98/10794 A2 * | 3/1998 |
| WO | 00 76551 A | 12/2000 |

OTHER PUBLICATIONS

Kratz et al. A Novel Macromolecular Prodrug Concept . . . Journal of Medicinal Chemistry. Mar. 10, 2000, vol. 43, No. 7, pp. 1253-1256.*
Yasuzawa et al. Structural Determination of the Conjugate of Human Serum Albumin with a Mitomycin C Derivative . . . Bioconjugate Chemistry. 1997, vol. 8, No. 3, pp. 391-399.*
Daniele Derossi, Gerard Chassaing and Alain Prochiantz; Trojan peptides: the penetratin system for intracellular delivery; trends in Cell Biology (vol. 8) Feb. 1998; 1998 Elsevier Science Ltd.; pp. 84-87.
Willner et al.; (6-Maleimidocaproyl) hydrazone of Doxorubicin-A New Derivative for the Preparation of Immunoconjugates of Doxorubicin; Bioconjugate Chem. 1993, 4, 521-527, pp. 521-527.
Firestone et al.; Synthesis and antitumor activity o f the immunoconjugate BR96-Dox; 1996 Elsevier Science B.V.; Journal of Controlled Release 39 (1996) 251-259.
Kratz et al.; "Preparation, Characterization and In Vitro Efficacy of Albumin Conjugates of Doxorubicin;" Biological & Pharmaceutical Bulletin (of Japan), JP, Pharmaceutical Society of Japan, Bd. 21, Nr. 1, 1998, Seiten 56-61, XP000738275 ISSN: 0918-6158; Abbildung.
A. Trouet et al.; "A covalent linkage between daunorubicin and proteins that is stable in serum and reversible by lysosomal hydrolases, as required for a lysosomotrope drug-carrier conjugate; In vitro and in vivo studies," Proceedings of the National Academy of Sciences of USA, Bd. 79, Jan. 1982, Seiten 626-629, XP002161367 Washington US.
S. Netzel-Arnett: "Comparitive sequence specificities of human 72- and 92-kDa gelatinases (type iv Collagenases) and Pump (Matrilysin)" Biochemistry, Bd. 32, Nr. 25, 1993, Seiten 6427-6432, XP002162368 Easton, PA UA.
M. Nichifor et al.; "Macromolecular prodrugs of 5-fluorouracil. 2: Enzymatic degradation." Journal of Controlled Release, Bd. 39, 1996, Seiten 79-92, XP002162369 Amsterdam NL.
G.M. Dubowchik et al.: "Cathepsin B-sensitive dipeptide prodrugs. 1. A model study of structural requirements for efficient release of doxorubicin," Bioorg Med Chem Lett., Bd. 8, Nr. 23, Dec. 1998, Seiten 3341-3346, XP002162370 Seite 3342; Tabelle 1.

* cited by examiner

*Primary Examiner*—Jeffrey E Russel
(74) *Attorney, Agent, or Firm*—Arthur S. Morgenstern; John B. Hardaway, III; Nexsen Pruet, LLC

(57) ABSTRACT

The invention relates to a carrier-drug conjugate comprising a carrier containing a polypeptide sequence having one or several cysteine radicals and a pharmacon containing a pharmaceutical and/or diagnostic active substance, a spacer molecule and a thiol binding group, whereby over 0.7 mol pharmacon per mol of cysteine radical is bound to the carrier by the thiol binding group. The invention also relates to a method for the production of said conjugate and to medicaments and diagnostic kits containing said conjugate.

15 Claims, 4 Drawing Sheets t = 0 min

HSA-Cys³⁴-2 t = 30 min

HSA-Cys³⁴-2

DOXO-Gln-Gly-Ala-Ile

CARRIER-DRUG CONJUGATE

This invention relates to carrier-drug conjugates as well as methods for their preparation and medicaments that contain the conjugates.

Many of the drugs now used are low-molecular-weight compounds and exhibit a high plasma clearance or total body clearance after systemic administration. Furthermore, they penetrate into the tissue structures of the body by diffusion processes and exhibit, as a rule, a uniform biodistribution. The two properties result in only small quantities of the drug reaching the place of action, and the drug brings about side effects on the healthy tissues of the body because of its distribution. These disadvantages are especially marked in the case of such drugs as possess a high cytotoxic potential, such as cytostatics or immunosuppressants.

New derivatives or formulations that permit a more selective therapy are therefore sought. To this end, chemoimmunoconjugates, or protein conjugates or polymer conjugates made up of a suitable carrier substance and a drug, are being developed.

With regard to the related art in this area, mention should be made of polymer conjugates in which cytostatics are coupled to serum proteins, antibodies, growth factors, hormone-like or peptide-like structures, or synthetic polymers (Mägerstädt, M., Antibody Conjugates and Malignant Disease, Library of Congress, 1990; Seymour, L. W., *Crit. Rev. Ther. Drug Carrier Sys.* (1992), 9, 135-187; Maeda, H., and Matsumura, Y., *Crit. Rev. Ther. Drug Carrier Sys.* (1989), 6, 193-210).

DE-A-41 22 210 describes conjugates of tumor-active compounds with albumin, the tumor-active compound being activated with N-hydroxysuccinimide and carbodiimide and the mixture so obtained being coupled directly to the carrier protein. The disadvantages of these conjugates are, among other things, that they cannot be obtained in the requisite high purity, the native structure of the albumin often does not remain intact on account of the preparation method, and the stoichiometric ratio of drug to albumin is inconstant and poorly reproducible. Furthermore, these conjugates do not allow of being released in suitable fashion in the target tissue or in the target cells.

It is therefore an object of the present invention to provide new carrier-drug conjugates that overcome the disadvantages of the conjugates known heretofore.

This object is achieved through the embodiments of the present invention characterized in the Claims.

In particular, there is provided a carrier-drug conjugate made up of a carrier, which contains a polypeptide sequence having one or a plurality of cysteine groups, and a drug, which contains a pharmaceutically and/or diagnostically active substance, a spacer molecule, and a thiol-binding group, more than 0.7 mol, preferably at least 0.9 mol, of drug per mol of cysteine group being bound to the carrier via the thiol-binding group. The expression "pharmaceutically active substance" means that the substance in question brings about a pharmacological effect either by itself or after its conversion by metabolism in the organism in question, and thus also includes the derivatives resulting from these conversions. Naturally, the pharmaceutically active substance can exhibit a single (for example as a cytostatic only) or a broad pharmacological action spectrum (for example as a cytostatic and as an antiphlogistic). The expression "diagnostically active substance" means that the substance in question can be detected, preferably also quantified, in the organism or parts thereof, such as for example cells and/or fluids, such as for example the serum, through suitable chemical and/or physical measurement methods.

The release of the pharmaceutically active substance is preferred because, as a rule, the low-molecular-weight active substance must interact with the target molecule in order to bring its pharmacological effectiveness into play. In the case of diagnostically active substances, as a rule, release of the diagnostic drug bound to the carrier molecule is not necessary but nevertheless can take place. According to the invention, therefore, a diagnostically active substance in particular can additionally be bound to the spacer molecule via a bond not cleavable in the body or directly to the carrier molecule-binding group.

According to a preferred embodiment of the conjugate according to the invention, the carrier is native or recombinant albumin.

The drug or the drug derivative in the conjugate according to the invention can be represented, for example, by the following scheme (AS, pharmaceutically and/or diagnostically active substance; SM, spacer molecule; TG, thiol-binding group):

The conjugate according to the invention represents a transport and/or depot form of the pharmaceutically

and/or diagnostically active substance, which thus reaches the target cells or the target tissue of the drug in targeted manner or in metered form. In contrast to the previously known conjugates, the conjugates of the present invention can be obtained in a high purity, the native structure of the carrier remains intact, and the stoichiometric ratio of drug to carrier is constant and reproducible.

In contrast to the albumin-cytostatic conjugates described in DE-A-41 22 210, the conjugate according to the invention further has the advantage that a spacer molecule is present between the pharmaceutically and/or diagnostically active substance and the thiol-binding group, which spacer molecule is tailored such that the pharmaceutically and/or diagnostically active substance or a corresponding active derivative thereof can be released hydrolytically and/or in pH-dependent fashion and/or enzymatically in the target tissue or in the target cells.

Carriers such as for example albumin or its drug conjugates exhibit a markedly long half-life in the systemic circulation (up to 19 days—Peters, T., Jr. (1985): Serum Albumin, *Adv. Protein. Chem.* 37, 161-245). Because of an elevated permeability of vessel walls of the malignant, infected or inflamed tissue for macromolecules, the carrier such as for example serum albumin passes preferentially into the target tissue (Maeda, H., and Matsumura, Y., *Crit. Rev. Ther. Drug Carrier Sys.* (1989), 6, 193-210). As a result, an active substance coupled to a carrier, for example albumin, can reach the place of action in more targeted fashion. Furthermore, the carrier-drug conjugate according to the invention prevents the pharmaceutically and/or diagnostically active substance from diffusing into healthy tissue structures of the body or from being eliminated via the kidney or injuring the kidney as much as the unbound pharmaceutically and/or diagnostically active substance. As a result, the pharmacokinetic profile of the pharmaceutically and/or diagnostically active substance is modified and improved, because the action of the pharmaceutically and/or diagnostically active substance is increased by a buildup at the place of action and, at the same time, the toxic effects on healthy systems of the body are diminished.

The conjugate of the present invention has excellent solubility in water. Furthermore, the conjugate according to the invention shows, in vivo, for example, an improved antitumoral effectiveness in comparison to the unbound pharmaceutically and/or diagnostically active substance.

According to a preferred embodiment of the conjugate according to the invention, the spacer molecule and/or the linkage between the pharmaceutically and/or diagnostically active substance and the spacer molecule and/or the linkage between the thiol-binding group and the spacer molecule is cleavable hydrolytically and/or in pH-dependent fashion and/or enzymatically. Preferably, the spacer molecule and/or the linkage between the pharmaceutically and/or diagnostically active substance and the spacer molecule and/or the linkage between the thiol-binding group and the spacer molecule contains at least one acid-labile bond. Examples of acid-labile bonds are ester, acetal, ketal, imine, hydrazone, carboxylhydrazone and sulfonylhydrazone bonds and bonds containing a trityl group. Bonds cleaved by hydrolysis with release of the pharmaceutically and/or diagnostically active substance are, for example, ester bonds or metal-complex compounds, such as are present in platinum-dicarboxylate complexes, where a diaminediaquo-platinum(II) complex is liberated. Examples of bonds not cleavable in the body, which may be present for example in the case of linkage to a diagnostically active substance, are amide bonds, saturated and unsaturated carbon-carbon bonds or bonds between carbon and a heteroatom, —C—X—, where X is preferably O, N, S or P.

According to a further embodiment of the conjugate according to the invention, the spacer molecule and/or the linkage between the pharmaceutically and/or diagnostically active substance and the spacer molecule and/or the linkage between the thiol-binding group and the spacer molecule contains at least one peptide bond. The peptide bond preferably lies within a peptide sequence that contains at least one cleavage sequence of a protease. The at least one peptide bond can therefore be implemented by the insertion of a peptide sequence into the spacer molecule and/or into the linkage between the pharmaceutically and/or diagnostically active substance and the spacer molecule and/or into the linkage between the thiol-binding group and the spacer molecule; that is, the linkage in question is a peptide bond and is preferably made up of about 1 to 30 amino acids. The peptide sequence is thus preferably tailored to the substrate specificity of certain of the body's own enzymes or of enzymes that occur in or are formed by microorganisms. In this way, the peptide sequence or a part of this sequence is recognized in the body by the enzymes and the peptide is cleaved.

The enzymes are, for example, proteases and peptidases, for example matrix metalloproteases (MMP), cysteine proteases, serine proteases and plasmin activators, which are formed or actived in intensified manner in diseases such as rheumatoid arthritis or cancer, leading to excessive tissue degradation, inflammations and metastasis. Target enzymes are in particular MMP 2, MMP 3 and MMP 9, which take part in the cited pathological processes as proteases (Vassalli, J., and Pepper, M. S. (1994), *Nature* 370, 14-15; Brown, P. D. (1995), *Advan. Enzyme Regul.* 35, 291-301).

Further proteases that represent target enzymes for conjugates of the present invention are cathepsins, in particular cathepsin B and H, which have been identified as key enzymes in inflammatory and malignant diseases (T. T. Lah et al. (1998), *Biol. Chem.* 379, 125-301).

According to a further embodiment of the conjugate according to the invention, the spacer molecule and/or the linkage between the pharmaceutically and/or diagnostically active substance and the spacer molecule and/or the linkage between the thiol-binding group and the spacer molecule contains at least one bond that is enzymatically cleavable but is not made up of a peptide bond. Examples are carbamate bonds, in which the active substance or a derivative of the active substance is released by cleavage with disease-specific enzymes, for example glutathione S-transferases, glucuronidases, galactosidases. It is also immediately possible that an enzymatically cleavable bond is built up from a peptide sequence and one of the aforenamed bonds that is not a peptide bond.

All the cited types of bond—hydrolytically cleavable bond, acid-labile bond, peptide bond, enzymatically cleavable bond not containing a peptide bond, and bond built up from a peptide sequence and a non-peptide bond—guarantee that the pharmaceutically and/or diagnostically active substance or a correspondingly active derivative is cleaved extracellularly and/or intracellularly at the place of action and the substance can bring its pharmaceutical and/or diagnostic action into play.

According to a preferred embodiment, the pharmaceutically active substance is a cytostatic, a cytokine, an immunosuppressant, an antirheumatic, an antiphlogistic, an antibiotic, an analgesic, a virostatic or an antimycotic. Especially suitable cytostatics of the conjugates of the present invention are the N-nitrosoureas such as nimustine, the anthracyclines doxorubicin, daunorubicin, epirubicin, idarubicin, mitoxantrone and ametantrone as well as related derivatives; the alkylating agents chlorambucil, bendamustine, melphalan and oxazaphosphorines as well as related derivatives; the antimetabolites, for example purine antagonists or pyrimidine antagonists, and folic acid antagonists such as methotrexate, 5-fluorouracil, 2'-deoxy-5-fluorouridine and thioguanine as well as related derivatives; the taxanes paclitaxel and docetaxel as well as related derivatives; the camptothecins topotecan, irinotecan, 9-aminocamptothecin and camptothecin as well as related derivatives; the podophyllotoxin derivatives etoposide, teniposide and mitopodozide as well as related derivatives; the Vinca alkaloids vinblastine, vincristine, vindesine and vinorelbine as well as related derivatives; calicheamicins; maytansinoids; and cis-configured platinum (II) complexes of the general formulas I to XII:

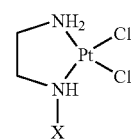

Formula I

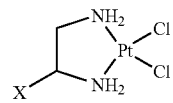

Formula II

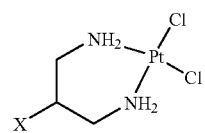

Formula III

Formula IV

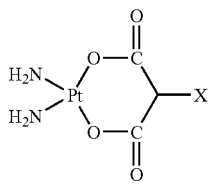

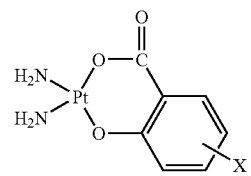

Formula XI

Formula V

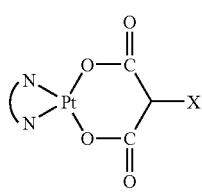

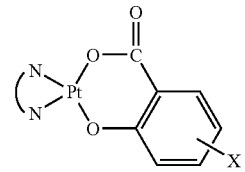

Formula XII

Formula VI

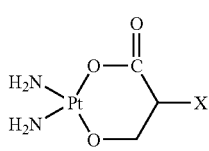

Formula VII

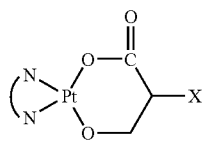

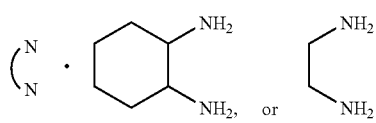

Formula IX

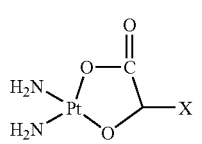

Formula X

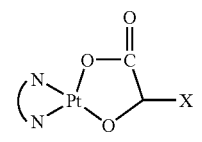

where X is the spacer molecule or the thiol-binding group.

Especially suitable cytokines in conjugates of the present invention are, for example, interleukin 2, interferon α-2a, interferon α-2b, interferon β-1a, interferon β-1b, interferon γ-1b and related derivatives. The cytokines used are, as a rule, medicaments prepared using genetic engineering.

Especially suitable immunosuppressants in conjugates of the present invention are, for example, cyclosporin A, FK 506 and related derivatives.

Especially suitable antirheumatics in conjugates of the present invention are, for example, methotrexate, sulfasalazine, chloroquine and related derivatives.

Especially suitable antiphlogistics and/or analgesics in conjugates of the present invention are, for example, salicylic acid derivatives such as for example acetylsalicylic acid and related derivatives; drug derivatives having an acetic or propionic acid group such as diclofenac or, respectively, indomethacin or ibuprofen or, respectively, naproxen; and aminophenol derivatives such as for example paracetamol.

Especially suitable antimycotics in conjugates of the present invention are, for example, amphotericin B and related derivatives.

Preferred virostatics in conjugates of the present invention are, for example, nucleoside analogs such as acyclovir, ganciclovir, idoxuridine, ribavirin, vidaribine, zidovudine, didanosine and 2',3'-dideoxycytidine (ddC) and related derivatives, as well as amantadine.

Preferred antibiotics in the conjugate according to the invention are sulfonamides, for example sulfanilamide, sulfacarbamide and sulfamethoxydiazine and related derivatives; penicillins, for example 6-aminopenicillanic acid, penicillin G as well as penicillin V and related derivatives; isoxazolylpenicillins such as oxacillin, cloxacillin and flucloxacillin as well as related derivatives; α-substituted benzylpenicillins such as ampicillin, carbenicillin, pivampicillin, amoxicillin and related derivatives; acylaminopenicillins, for example mezlocillin, azlocillin, piperacillin, apalcillin and related derivatives; amidinopenicillins, for example mecillinam; atypical β-lactams such as imipenam and aztreonam; cephalosporins, for example cephalexin, cefradin, cefaclor, cefadroxil, cefixime, cefpodoxime, cefazolin, cefazedone, cefuroxime, cefamandole, cefotiam, cefoxitin, cefotetan, cefmetazole, latamoxef, cefotaxime, ceftriaxone, ceftizoxime, cefmonoxime, ceftazidime, cefsulodin and cefoperazone as well as related derivatives; tetracyclines such as tetracycline, chlorotetracycline, oxytetracycline, demeclocycline, rolitetracycline, doxycycline, minocycline and related derivatives; chloramphenicols such as chloramphenicol and thiamphenicol as well as related derivatives; gyrase inhibitors, for example nalidixic acid, pipemidic acid, norfloxacin, ofloxacin, ciprofloxacin and enoxacin as well as related derivatives; and antituberculotics such as isoniazid and related derivatives.

Of course, a single drug species (for example a drug with a cytostatic as pharmaceutically active substance) or various drug species (for example a plurality of distinct cytostatics or a cytostatic and an antiphlogistic, etc., as pharmaceutically active substance) can be present in combined form per mole in the conjugate according to the invention.

According to a further preferred embodiment of the conjugate according to the invention, the spacer molecule contains a substituted or unsubstituted, branched-chain or straight-chain aliphatic alkyl group with 1 to 12 carbon atoms Drugs or drug derivatives, having an HOOC group, of the conjugates according to the invention can be derivatized, for example, in the following way:

Esterification here is effected with methods known in the related art.

It is further possible to convert the HOOC group to a hydrazide group, for example by reaction with tert-alkylcarbazates followed by cleavage with acids (described in DE-A-196 36 889), and to react the drug, having a hydrazide group, with a group containing a carbonyl component and made up of the thiol-binding group and the spacer molecule, as is

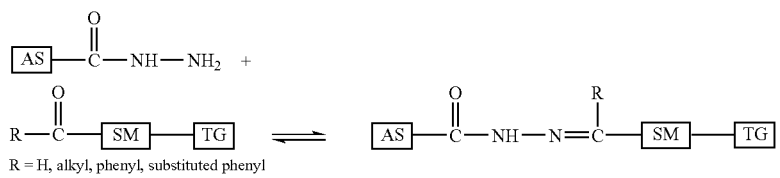

and/or at least one substituted or unsubstituted aryl group and/or an aliphatic carbon ring with 3 to 12 carbon atoms. The aliphatic alkyl group preferably contains 1 to 20 carbon atoms, which may in part be replaced by oxygen atoms in order, for example, to increase the solubility in water, such groups preferably being derived from an oligoethylene oxide or oligopropylene oxide chain. Especially suitable groups that are derived from oligoethylene oxide or oligopropylene oxide chains include, for example, diethylene glycol chains, triethylene glycol chains and dipropylene glycol chains. A preferred aryl group is an unsubstituted or substituted phenyl group in which, likewise, one or a plurality of carbon atoms may be replaced by heteroatoms. Preferred substituents of the aliphatic alkyl group or of the aryl group are hydrophilic groups such as sulfonic acid groups, aminoalkyl groups and hydroxy groups.

Preferred diagnostically active substances of the conjugate according to the invention include, for example, one or a plurality of radionuclides; one or a plurality of ligands containing radionuclides, preferably complexing such radionuclides; one or a plurality of positron emitters; one or a plurality of NMR contrast media; one or a plurality of fluorescing compound(s); or one or a plurality of contrast media in the near IR region.

In a further preferred embodiment of the conjugate according to the invention, the thiol-binding group contains a maleinimide group, a haloacetamide group, a haloacetate group, a pyridyldithio group, a vinylcarbonyl group, an aziridine group, a disulfide group or an acetylene group, which are substituted if appropriate.

The drug or drug derivative of the conjugates according to the invention can be prepared according to one of the following general descriptions, depending on what functional group is present.

described, among others, in DE-A-196 36 889:

Drugs or drug derivatives, having an $H_2N$ group, of the conjugates according to the invention can be derivatized, for example, in the following way:

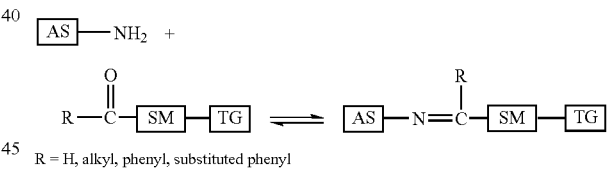

The reaction to the imine derivatives here is effected with methods known in the related art.

Drugs or drug derivatives, having an HO group, of the conjugates according to the invention can be derivatized, for example, in the following way:

Esterification here is effected with methods known in the related art.

Drugs or drug derivatives, having a carbonyl component, of the conjugates according to the invention can be derivatized, for example, in the following way:

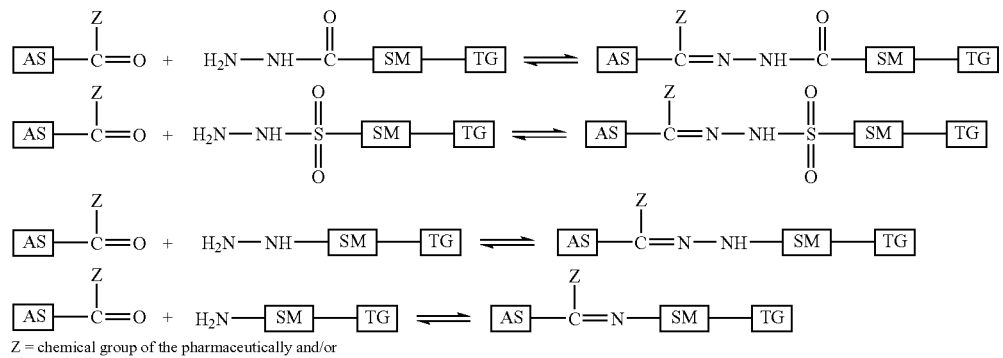

Z = chemical group of the pharmaceutically and/or diagnostically active substance The reaction to the carboxyhydrazone, sulfonylhydrazone, hydrazone or imine derivatives here is effected with methods known in the related art.

It is further possible to convert an HO group or an NH$_2$ group of a pharmaceutically and/or diagnostically active substance to a carbonyl component, for example by esterification or amidation with a carboxylic acid-bearing carbonyl component, according to the following general reaction schemes,

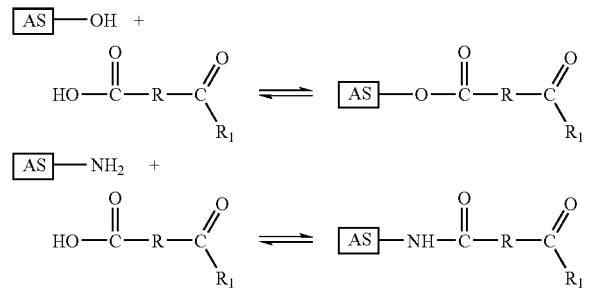

where R is an aliphatic carbon chain and/or an aliphatic carbon ring and/or an aromatic and R$_1$=H, alkyl, an unsubstituted phenyl group or a substituted phenyl group. R preferably contains 1 to 12 carbon atoms, which may likewise be substituted, for example by hydrophilic groups such as sulfonic acid groups, aminoalkyl groups or hydroxyl groups. The aromatic is preferably a benzene ring, which may likewise be substituted. Preferred substituents are, for example, the above-named hydrophilic groups.

The carbonyl component can furthermore be introduced by other chemical reactions, for example by electrophilic substitution on the HO or NH$_2$ group of the active substance with a suitable carbonyl component.

The drugs derivatized in this way, which now have a carbonyl component, are converted to the corresponding carboxylhydrazone, sulfonylhydrazone, hydrazone or imine derivatives in a fashion analogous to the above-described methods with carrier molecule-binding spacer molecules having an amino group, hydrazide group or hydrazine group. The cleavage of these acid-labile bonds afterward leads to a release of derivatized pharmaceutically and/or diagnostically active substance having a carbonyl component.

The groups that are made up of the thiol-binding group and the spacer molecule can be prepared, for example, according to methods that are described in, among others, DE-A-196 36 889, U. Beyer et al. 1997 (*Chemical Monthly*, 128, 91, 1997), R. S. Greenfield et al., 1990 (*Cancer Res.*, 50, 6600, 1990), T. Kaneko et al., 1991 (*Bioconjugate Chem.*, 2, 133, 1991), Bioconjugate Techniques (G. T. Hermanson, Academic Press, 1996), or in U.S. Pat. No. 4,251,445.

Drugs or drug derivatives, containing a peptide bond, of the conjugates according to the invention can be prepared, for example, by reacting a peptide that is made up of 2 to about 30 amino acids with a thiol-binding compound, so that a thiol-binding group is introduced directly or via a spacer molecule at the N-terminal end of the peptide. The synthesis of such carrier molecule-binding peptide derivatives is preferably effected by a solid-phase synthesis known to one skilled in the art, a carboxylic acid-bearing, carrier molecule-binding spacer molecule, for example a maleinimide carboxylic acid, being bound by peptide coupling to the N-terminal end of the peptide in the last step of peptide assembly and the carrier molecule-binding peptide then being split off from the solid phase.

In the presence of a condensation agent such as for example N,N'-dicyclohexylcarbodiimide (DCC) or N-cyclohexyl-N'-(2-morpholinoethyl)carbodiimide methyl-p-toluenesulfonate (CMC) or 1-benzotriazolyloxytris(pyrrolidino)phosphonium hexafluorophosphate (PyBOP) or benzotriazolyl-N,N,N',N'-tetramethyluronium hexafluorophosphate, and if appropriate with the addition of N-hydroxysuccinimide or of a water-soluble N-hydroxysuccinimide such as for example N-hydroxysuccinimide-3-sulfonic acid sodium salt, or 1-hydroxybenzotriazole, and/or in the presence of a base, for example N-methylmorpholine or triethylamine, the peptide derivatives so obtained can be reacted to the corresponding thiol-binding drug-peptide derivatives with drugs or drug derivatives that have an H$_2$N or HO group:

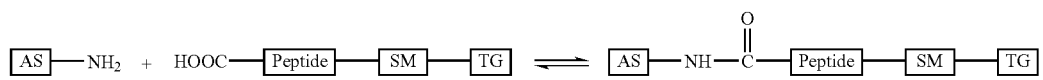

-continued

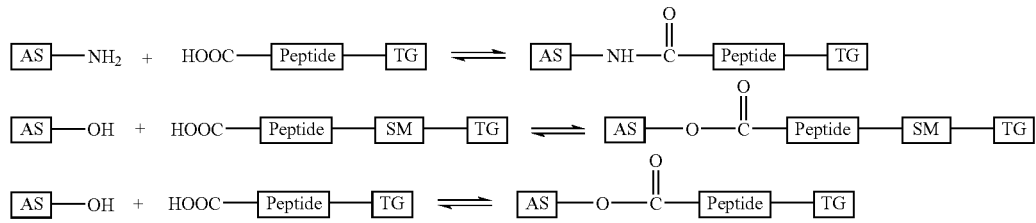

It is further possible, via the HOOC group of the drugs of the conjugates according to the invention, to introduce an H$_2$N or HO group, for example by derivatization via the α-amino group of the amino acids lysine, serine or threonine or with a diamino compound of the general formula H$_2$N—(CH$_2$)$_n$—NH$_2$ or an alcoholamine of the general formula H$_2$N—(CH$_2$)$_n$—OH with n=1 to 12, and then to react these derivatives with the above-cited peptide derivatives to the corresponding thiol-binding drug-peptide derivatives:

J. Cancer 49, 341-346, Lah, T. T., and Kos, J. (1998), Biol. Chem. 22 379, 125-130).

For example, octapeptides (P$_4$-P'$_4$) for MMP 2 and MMP 9 have been identified (see Table 1), which octapeptides simulate the cleavage sequence of the collagen chain and are cleaved with particular efficiency by MMP 2 and 9 (in what follows, amino acids are abbreviated in accordance with the international three-letter code):

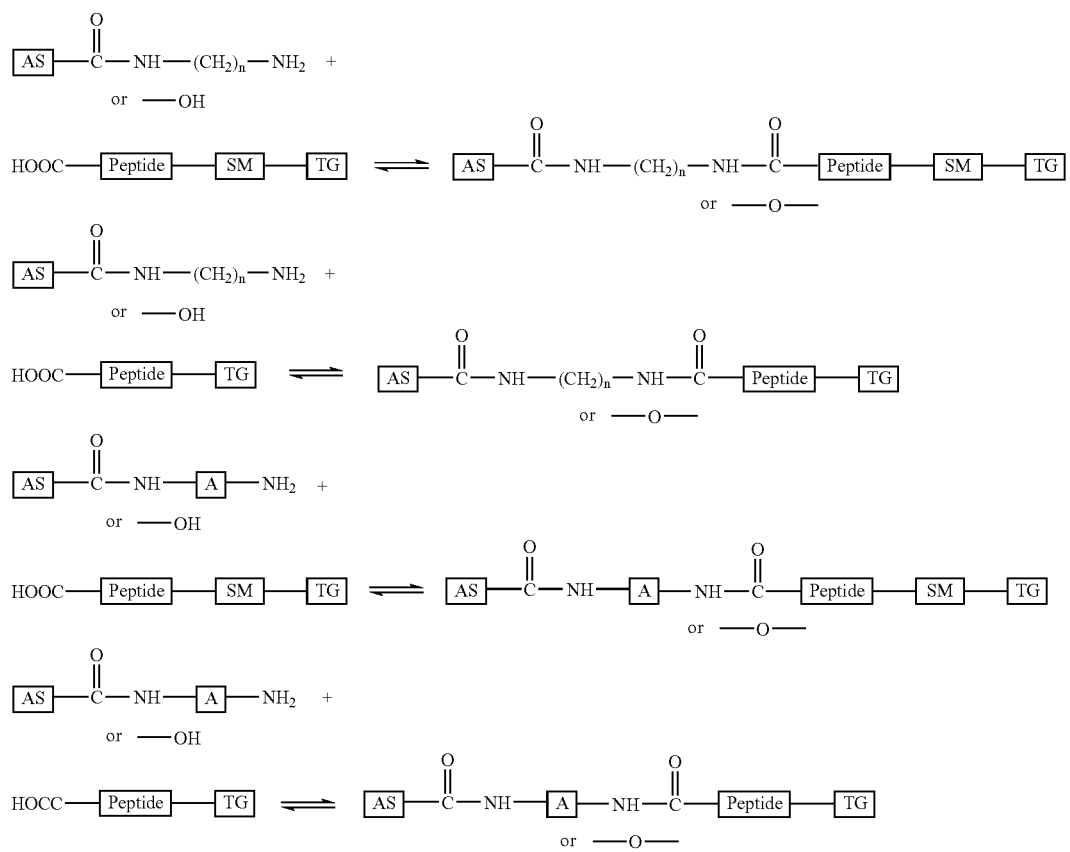

A = lysine, serine or threonine

The substrate specificity of target enzymes such as for example of MMP 2, MMP 3, MMP 9, cathepsin B and H is known (Netzel-Arnett et al. (1993), Biochemistry 32, 6427-6432, Shuja, S., Sheahan, K., and Murname, M. J. (1991), Int.

TABLE 1

| Peptide | | | | | | | |
|---|---|---|---|---|---|---|---|
| P$_4$ | P$_3$ | P$_2$ | P$_1$ | P'$_1$ | P'$_2$ | P'$_3$ | P'$_4$ |

Gly-Pro-Leu-Gly-Ile-Ala-Gly-Gln [SEQ. ID No. 1]
Gly-Pro-Gln-Gly-Ile-Trp-Gly-Gln [SEQ. ID No. 2]

(Netzel-Arnett et al., *Biochemistry* 32, 1993, 6427-6432)

The peptides are enzymatically cleaved exclusively at the $P_1$-$P'_1$ bond.

Furthermore, in the case of cathepsin B, substrate-specific peptides are known with the sequence -Gly-Phe-Leu-Gly- SEQ. ID No. 3

-Gly-Phe-Ala-Leu- SEQ. ID No. 4

-Ala-Leu-Ala-Leu- SEQ. ID No. 5

-Arg-Arg- or -Phe-Lys-

Werle, B., Ebert, E., Klein, W., and Spiess, E. (1995), *Biol. Chem. Hoppe-Seyler* 376, 157-164; Ulricht, B., Spiess, E., Schwartz-Albiez, R., and Ebert, W. (1995), *Biol. Chem. Hoppe-Seyler* 376, 404-414).

The peptide sequence that contains intended peptide cleavage points relevant for the target enzyme can also be constructed such that the intended peptide cleavage point is repeated a plurality of times, for example by:

-Gly-Pro-Leu-Gly-Ile-Ala-Gly-Gln-Gly-Pro-Leu-Gly-Ile-Ala-Gly-Gln SEQ ID No. 6 or

-Phe-Lys-Phe-Lys-Phe-Lys-Phe-Lys-Phe-Lys-Phe-Lys-
SEQ. ID No. 7 or a repetitive peptide sequence can be integrated that increases the distance between the thiol-binding group and the relevant intended peptide cleavage point, as for example by:

-(Gly)$_n$-Phe-Lys-Phe-Lys- SEQ ID No. 8 and 10-27 with, preferably, n=2 to 20, more preferably n≦12.

An important feature of this embodiment of the conjugate according to the invention is that the intended peptide cleavage point relevant for the target enzyme in question is present at least once in an oligopeptide made up of roughly 1 to 30 amino acids. The above-cited oligopeptides are representative examples for the enzymatically cleavable bond in the conjugates according to the invention and do not restrict the invention.

Drugs or drug derivatives, containing a cytokine, of the conjugate according to the invention can be prepared for example, by reacting the cytokine with a space molecule containing a thiol-binding group, which space molecule exhibits a carboxylic acid or and activated carboxylic acid.

If the spacer molecule exhibits an N-hydroxysuccinimide ester group (N-hydroxysuccinimide or N-hydroxysuccinimide-3-sulfonic acid sodium salt), it is reacted directly with the cytokine. The reaction of the cytokine with a spacer molecule containing a thiol-binding group, which spacer molecule exhibits a carboxylic acid, to the corresponding thiol-binding derivatives takes place in the presence of a condensation agent, such as for example N,N'-dicyclohexylcarbodiimide (DCC) or N-cyclohexyl-N'-(2-morpholinoethyl)-carbodiimide methyl-p-toluene sulfonate (CMC), and if appropriate with the addition of N-hydroxysuccinimide or N-hydroxysuccinimide-3-sulfonic acid sodium salt. As a rule, the cytokines derivatized in this way are purified with the aid of gel chromatography. The above-described reactions are well known to a person skilled in the art (see, e.g., Bioconjugate Techniques, G. T. Hermanson, Academic Press, 1996).

The above-described drugs or drug derivatives are coupled to a carrier containing a polypeptide sequence with one or a plurality of cysteine groups, such as for example native or recombinant albumin, so that more than 0.7 mol, preferably at least 0.9 mol, of drug per mol of cysteine group is bound to the carrier via the thiol-binding group. If the polypeptide sequence of the carrier contains n (for example 3) cysteine groups, this means that 1 mol of this carrier contains n (for example 3) mol of cysteine groups, and thus a maximum of n (for example 3) mol of drug can be present bound to the carrier per mol of the corresponding conjugate. In the conjugate according to the invention, therefore, 100% of the cysteine groups present in the carrier are ideally bound with a drug via the thiol-binding group.

A further embodiment of the present invention thus relates to a method for the preparation of a conjugate as defined above, including (i) treatment of the carrier with a reducing agent so that more than 0.7 mol, preferably at least 0.9 mol, of cysteine SH groups is present in the carrier per mol of cysteine group and (ii) coupling of the drug to the cysteine SH groups in the carrier via the thiol-binding group.

In a preferred embodiment of the method according to the invention, the reducing agent used for the treatment of the carrier is dithiothreitol (DTT), dithioerythritol (DTE) or mercaptoethanol. The especially preferred reducing agent is DTT.

The method according to the invention is based on the knowledge that the carriers known in the related art exist in an inhomogeneous oxidation state. For example, in the case of commercially available native albumin, as a rule, the Ellmann photometric assay detects≈0.2 to 0.7 mol of HS groups per mol of cysteine groups in the albumin; that is, the cysteine-34 is often oxidized by sulfur-containing compounds such as for example cysteine or glutathione via a disulfide bond. This means that the cysteine SH groups present in the albumin are at least often not free, which formerly led to the condition that the yield of prepared conjugates was too low and/or strongly fluctuating from one albumin charge to another albumin charge.

It has been established according to the invention that commercially available carriers can be treated with a reducing agent, the cysteine groups oxidized via disulfide bonds being reduced so that more than 0.7 mol of cysteine SH groups is present per mol of cysteine groups in the carrier. The

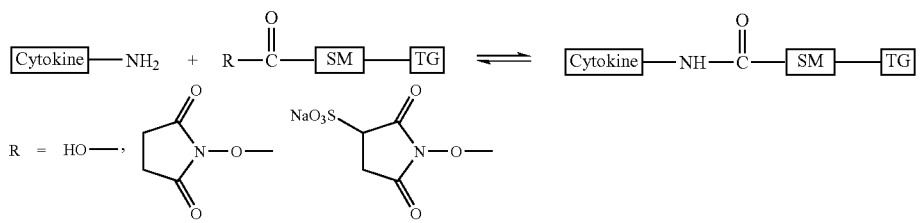

reaction is preferably controlled such that at least 0.9 mol of cysteine SH groups becomes available per mol of cysteine group in the carrier.

The reaction of the reducing agent with a commercially available carrier, for example albumin, takes place, for example, in a salt buffer, for example in 0.01 M sodium borate, 0.15 M NaCl, 0.001 M EDTA or 0.15 M NaCl, 0.004 M phosphate in a pH range of 5.0 to 8.0, preferably 6.0 to 7.0. The reducing agent can be inlet in excess; preferably the ratio of reducing agent to carrier is between 0.5:1 and 10:1. The reaction time is between 1 h and 96 h, preferably between 6 h and 24 h.

The carrier treated with the reducing agent is isolated, for example, by gel filtration (for example Sephadex® G10 or G25; solvent 0.004 M phosphate, 0.15 M NaCl, pH 7.4) or by ultrafiltration.

The concentration of carrier after gel filtration has been carried out is determined using the extinction coefficient at 280 nm; the number of HS groups inserted is determined with Ellmann's reagent at 412 nm. The carrier solution thus isolated can be used directly for the synthesis of the conjugates. It is also possible to concentrate the carrier solution with a commercially available concentrator or to lyophilize it. The isolated carrier solution or the lyophilizate can be stored in the temperature range of −78 to +30° C.

The coupling of the above-described drug derivatives to the carrier takes place, for example, at room temperature. To the carrier, which is in a salt buffer (for example 0.15 M NaCl, pH 6.0 to 8.0), which was previously degassed if appropriate, there is added a roughly 1.1-fold to 10-fold excess of the drug prepared as described above (relative to the number of HS groups present in the carrier), dissolved in a minimal quantity of solvent, for example DMF, dimethyl sulfoxide, water, salt buffer, ethanol, methanol, propylene glycol, glycerin, acetonitrile or THF (roughly 1 to 10% of the volume of the test portion of carrier). It is also possible to add the drug to the carrier solution as a solid. Furthermore, it may be advantageous to add an auxiliary agent, such as for example a fatty acid or a tryptophanate derivative, to the carrier solution. After a reaction time between 5 min and 48 h, the solution is centrifuged if necessary, and the carrier-drug conjugate formed is isolated by subsequent gel filtration (for example Sephadex® G10 or G25) in a salt buffer, such as for example 0.004 M phosphate, 0.15 M NaCl, pH 6.0 to 8.0.

The purity of the conjugate obtained can be verified, for example, by HPLC, for example by gel chromatography. In contrast to commercially available conjugates, the conjugates prepared according to a preferred embodiment of the method according to the invention exhibit a purity of more than 95%.

The solution of the conjugate so obtained can be concentrated with a commercially available concentrator. The conjugates can be stored in dissolved form at +1 to +30° C. or in frozen form at T=0° C. to −78° C. It is further possible to lyophilize the solution of the conjugates and to store the lyophilizate at +30° to −78° C.

A further embodiment of the present invention relates to a medicament containing a conjugate as defined above and, if appropriate, a pharmaceutically compatible carrier and/or auxiliary agent and/or a diluting agent. The medicament according to the invention can preferably be used for the treatment of cancer diseases, autoimmune diseases, acute or chronically inflammatory diseases, and diseases that are caused by viruses or microorganisms such as for example bacteria and/or fungi.

Yet a further embodiment of the present invention relates to a diagnostic kit including a conjugate as defined above. The diagnostic kit according to the invention can preferably be used for the detection of the diseases as above defined and/or for the detection of molecules of the carrier and/or their distribution in the body.

The following example explains the present invention in greater detail without restricting it.

EXAMPLE

Reaction of Human Serum Albumin (HSA) with Dithiothreitol (DTT)

The method for the treatment of HSA with a reducing agent is illustrated more exactly by the following example: 2.0 g of human serum albumin (10 mL of a 20% HSA solution, Pharma Dessau) is diluted with 10 mL of buffer A (0.004 M sodium phosphate, 0.15 M NaCl, pH 7.0) and added to 100 μL of a freshly prepared $0.036 \times 10^{-2}$ M solution of DTT (5.55 mg of DTT dissolved in 100 μL of buffer A), and the reaction vessel, tightly sealed to exclude air, is shaken for 16 h at room temperature. The albumin solution is then purified by gel filtration (5.0 cm×25.0 cm column, Sephadex® G25; solvent buffer 0.004 M sodium phosphate, 0.15 M NaCl, pH 7.4). The protein concentration after gel filtration was determined by photometry at 280 nm ($\epsilon(HSA)_{280}=35,700$ M$^{-1}$ cm$^{-1}$, c[HSA]≈$3.1\times10^{-4}$ M), and the number of HS groups introduced was determined with Ellmann's reagent at 412 nm ($\epsilon_{412}=13,600$ M$^{-1}$ cm$^{-1}$, c[HS groups]≈$3.07\times10^{-4}$ M). In the HSA thus treated, there is accordingly 0.99 mol of free cysteine SH groups per mol of cysteine group. The treated HSA was concentrated to roughly $1.0\times10^{-3}$ M (Centriprep-10®) and used directly for the coupling reaction, described in what follows, with a thiol-binding drug of the present invention.

Preparation of the Conjugate A-DOXO-HYD-C According to the Invention

The HSA-doxorubicin conjugate (A-DOXO-HYD-C), made up of HSA treated with DTT in accordance with the above example, and a maleinimidophenylacetic acid hydrazone derivative of doxorubicin (DOXO-HYD), was further prepared in the following way.

Structure of DOXO-HYD:

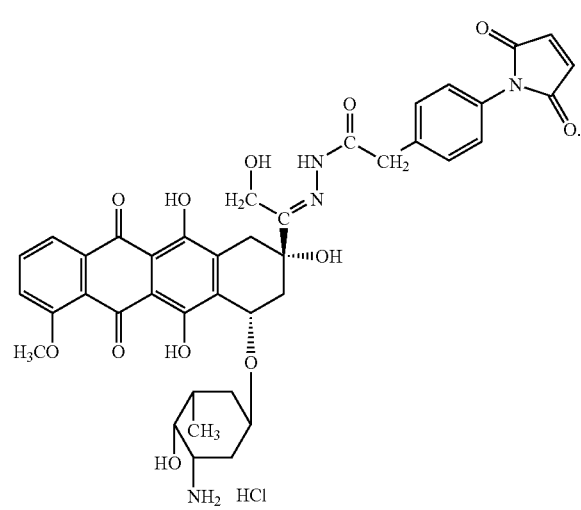

12 mL of the HSA test portion treated with DTT (sulfhydryl content of 0.99 mol per mol of HSA) was added to 0.6 mL of a solution of DOXO-HYD (Mr 807.8) in DMF (12.5 mg dissolved in 0.6 mL of DMF), and the reaction solution, sealed, was shaken for 18 h. The product HSA-doxorubicin conjugate was isolated using a Sephadex® G-25F column (column 5.0 cm×25 cm) (retention volume 85-135 mL). The quantity of bound doxorubicin was determined with the help of the extinction coefficient of doxorubicin at 495 nm ($495=10,650 M^{-1} cm^{-1}$ at pH 7.4). According to the determination, 0.97 mol of doxorubicin per mol of cysteine group in the HSA is bound to the HSA in this example.

Methods: FPLC for the preparation of the conjugates: P-500 pump, LCC 501 controller (Pharmacia) and LKB 2151 UV monitor. The protein concentration of the conjugate was determined photometrically and also by the BCA protein assay (Pierce, U.S.A.).

Figure 1A:
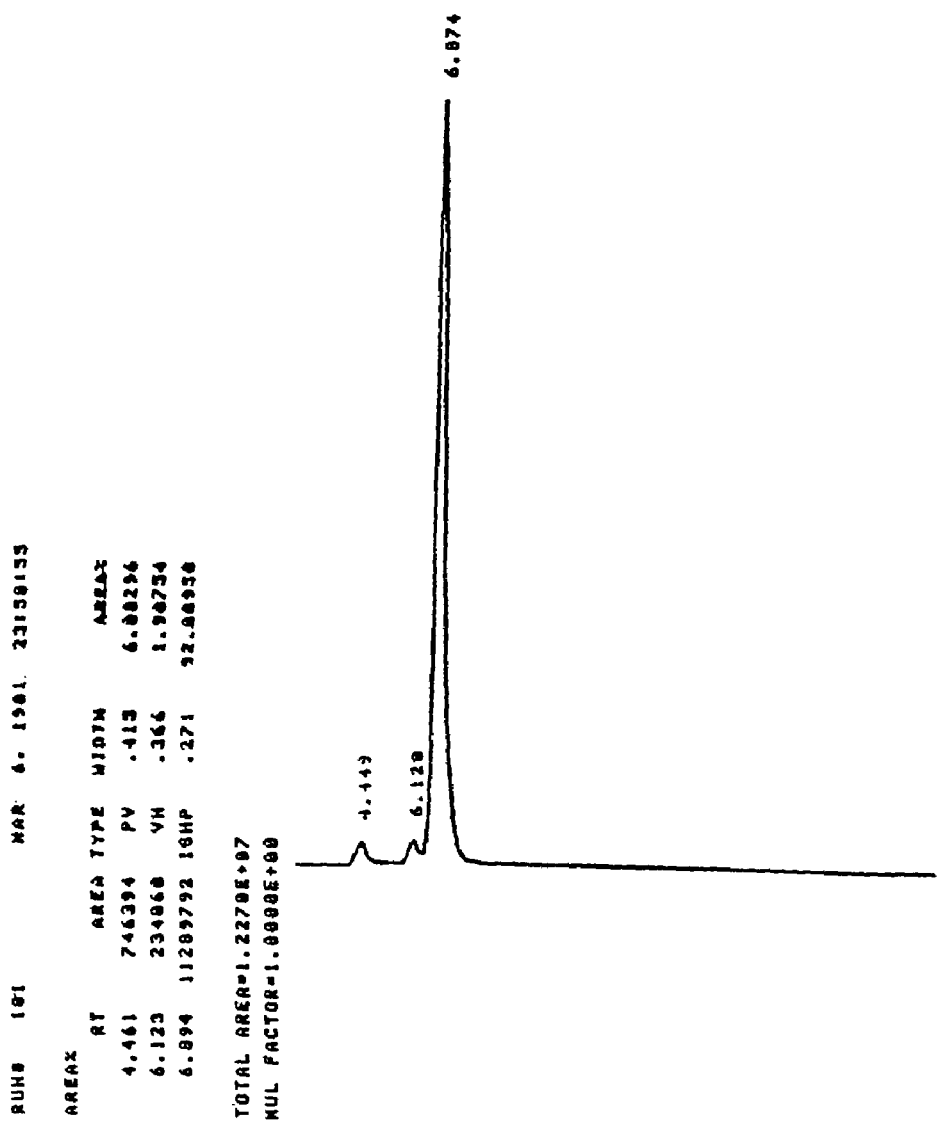
FIG. 1 (A) is an HPLC chromatogram of a conjugate according to the invention (A-DOXO-HYD-C). The plot shows the absorption at 495 nm versus the retention time in min. (B) is the corresponding HPLC chromatogram of commercially available native albumin (Immuno GmbH).
Figure 1B:
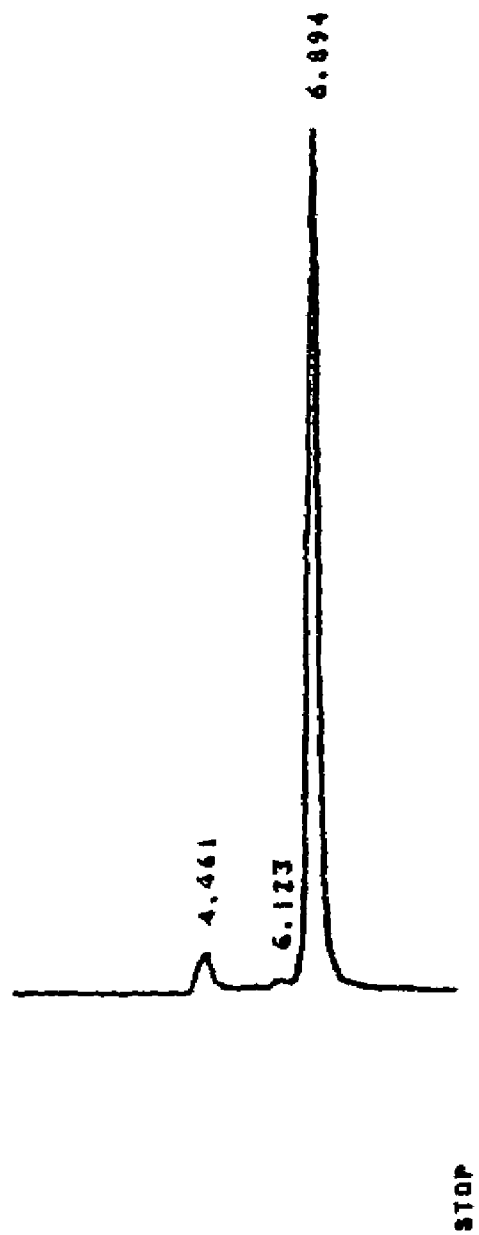

The purity of the A-DOXO-HYD-C conjugate was checked by HPLC with the aid of an analytical column (Bio-Sil SEC 250 (300 mm×7.8 mm), Bio-RAD (mobile phase, as a rule, 0.15 M NaCl, 0.01 M $NaH_2PO_4$, 5% $CH_3CN$, pH 7.0) at $\lambda=495$ nm. The HPLC chromatograms for A-DOXO-HYD-C and of commercially available native albumin (Immuno GmbH) are presented in FIG. 1A (A-DOXO-HYD-C) and FIG. 1B (native albumin). It can be clearly seen that A-DOXO-HYD-C exhibits an excellent purity, comparable with the commercially available native albumin.

Structure of A-DOXO-HYD-C:

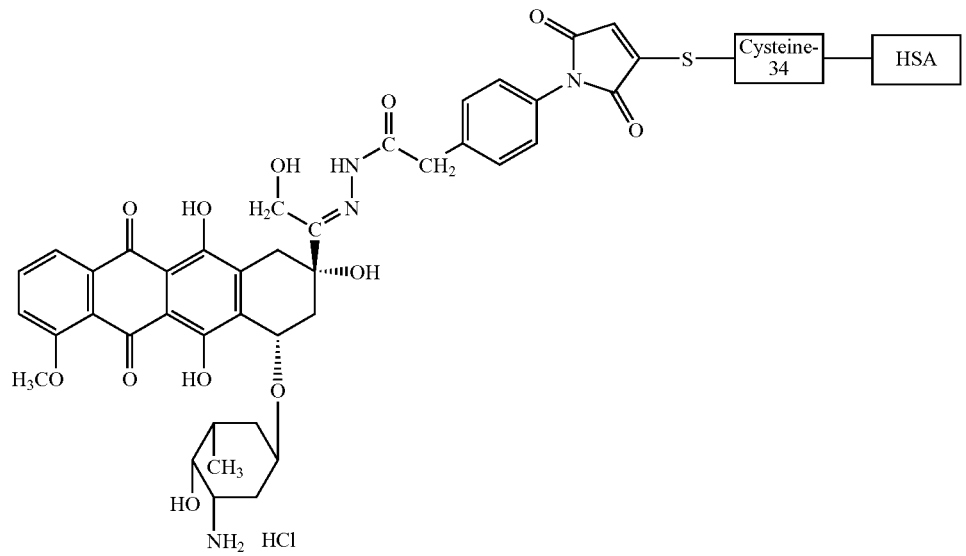

(HSA = human serum albumin)

Preparation of a Conjugate According to the Invention, Containing HSA Treated with DTT and a Doxorubicin-Maleinimide-Peptide Derivative Cleavable by MMP 9

The doxorubicin-maleinimide-peptide derivative (2) was prepared in accordance with the following reaction equation:

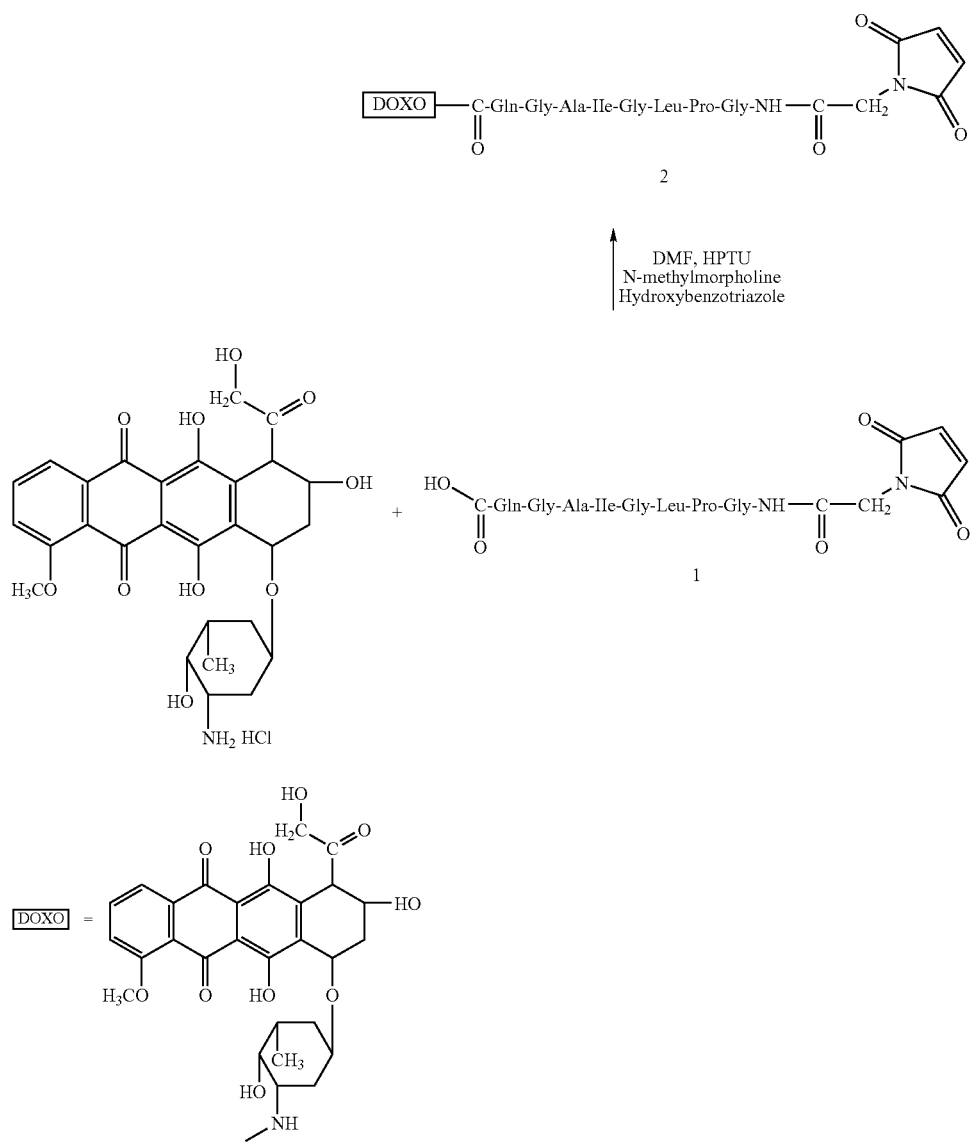

SEQ. ID No. 9

Here the octapeptide

Gln-Gly-Ala-Ile-Gly-Leu-Pro-Gly SEQ. ID No. 9 derivatized with maleinimidoglycine 1 (Mr 848, prepared by solid-phase synthesis by Bachem AG, Switzerland) was reacted with doxorubicin according to the following method:

To a slightly turbid solution of 17.1 mg of doxorubicin in 3 mL of DMF there are added 25 mg of 1 (as the trifluoroacetate salt) dissolved in 500 µL of DMF, 33.5 mg of O-benzotriaz- olyl-N,N,N',N'-tetramethyluronium hexafluorophosphate (HPTU) dissolved in 200 µL of DMF, 11.9 mg hydroxybenzotriazole hydrate dissolved in 100 µL of DMF, and 16.2 µL of N-methylmorpholine, and the charge is then agitated for 18 h at room temperature in darkness. DMF was removed under high vacuum, and the solid was taken up in 20 mL of methanol, filtered, and concentrated in vacuum to 1 mL. After purification with silica gel (acetate/methanol 2/1), 5 mg of 2 was obtained.

3.0 mL of an HSA test portion treated with DTT (sulfhydryl content of 0.95 per HSA molecule, content of HS groups 1000 µM) was added to a solution of 2 (Mr 1374) in DMF (5.1 mg dissolved in 250 µL of DMF), and the reaction solution, sealed, was shaken for 30 min. The product albumin-doxorubicin conjugate was isolated using a Sephacryl® HR100 column (2.0 cm×20 cm). In this way, the albumin conjugate (designated HSA-Cys$^{34}$-2 in what follows) of the following structure was isolated (exhaustion factor approximately 0.9):

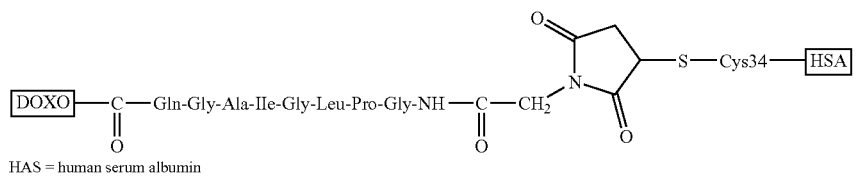

HAS = human serum albumin

SEQ. ID No. 9.

Figure 2A:
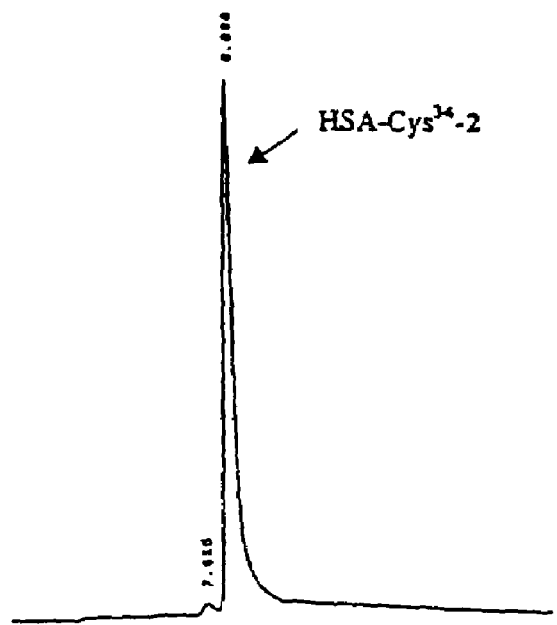
FIG. 2 shows HPLC chromatograms (gel chromatography, Biosil 250 SEC column, Biorad) of a conjugate according to the invention (HSA-Cys$^{34}$-2), which is cleavable by the matrix metalloprotease MMP 9. The absorption at 495 nm is also plotted versus the retention time in min. (A) Chromatogram of the conjugate HSA-Cys$^{34}$-2 before incubation with MMP 9 (t=0). (B) Chromatogram of the conjugate HSA-Cys$^{34}$-2 after incubation with MMP 9 for 30 min (t=30 min) and also showing a peak for fragment DOXO-Gln-Gly-Ala-Ile residues 1-4 of SEQ ID No. 9.
Figure 2B:
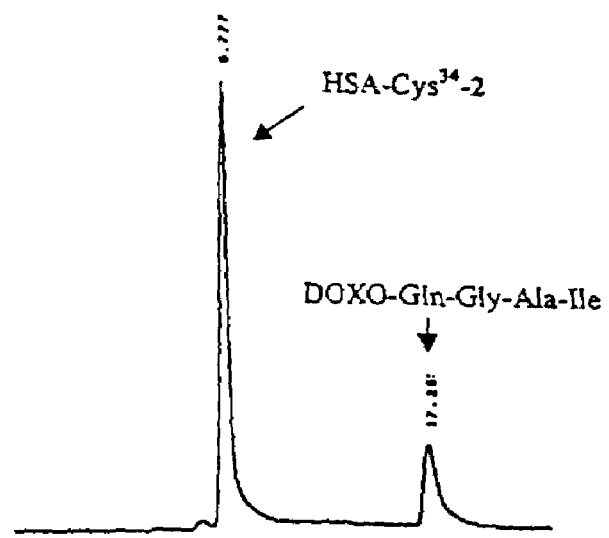

The peptide sequence Gln-Gly-Ala-Ile-Gly-Leu-Pro-Gly SEQ. ID No. 9 is recognized by the matrix metalloprotease MMP 9 and cleaved between isoleucine and glycine. This was shown by the following experiment: 200 μL of a 100 μM solution of HSA-Cys$^{34}$-2 was incubated for 30 minutes at 37° C. with trypsine/aprotinine-activated MMP 9 (2 mU, from Calbiochem, Germany). The liberation of DOXO-Gln-Gly-Ala-Ile due to cleavage with MMP 9 was confirmed by HPLC gel chromatography (Biosil 250 SEC column from Biorad, detection at λ=495 nm) before incubation (t=0, compare FIG. 2A) and after an incubation time of 30 minutes with activated MMP 9 (t=30, compare FIG. 2B).

Biological Studies

As an example for the in vivo effectiveness of the conjugates according to the invention, the biological data of the HSA-doxorubicin conjugate A-DOXO-HYD-C are presented.

In the "RENCA" (renal cell carcinoma) model, doxorubicin and the conjugate A-DOXO-HYD-C according to the invention were compared with each other with respect to antitumoral action at approximately equitoxic dose (intravenous therapy, 10 days after injection of roughly 1 million renal carcinoma cells into the left kidney).

Animals: Balb/c mice, female; tumor: RENCA, renal cell carcinoma; therapy: day (d) 10, 14, 18, 21 intravenous (i.v.); end of trial: d 25.

The results of these studies are summarized in Table 2.

TABLE 2

| Number of mice | Substance | Dose (mg/kg/inj.) | Mortality (d) | Average loss of body weight (%), d 1 to 25 |
|---|---|---|---|---|
| 10 | Control | | 2 | −14 |
| 10 | Albumin control | 4 × 1.4 g | 1 | −16 |
| 10 | Doxorubicin (doxo) | 4 × 6 mg/kg | 1 | −21 |
| 10 | A-DOXO-HYD-C | 4 × 12 mg/kg | 0 | −18 |

The dose is relative to the quantity of doxorubicin present. The dosages of doxorubicin and A-DOXO-HYD-C are approximately equitoxic (see loss of body weight in Table 2).

Figure 3A:
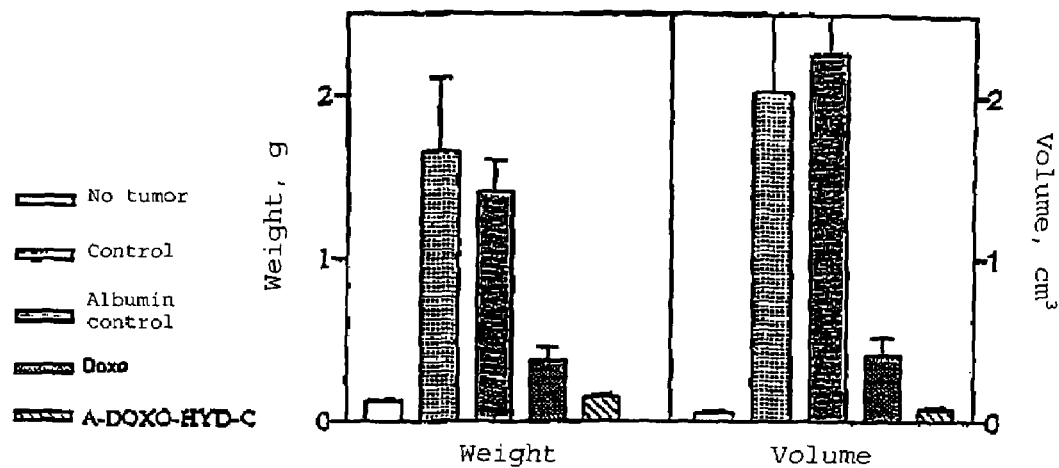
FIG. 3 shows the graphical representation of the weights and volumes of kidneys and renal tumors (A) as well as the lung weights and the number of pulmonary metastases (B) of mice in which a renal carcinoma was induced, and that were subjected to the cited treatments (control: no treatment; albumin control: native albumin; Doxo: doxorubicin; A-DOXO-HYD-C: conjugate according to the invention). For comparison, the data for mice not injected with tumor cells are also shown (no tumor).
Figure 3B:
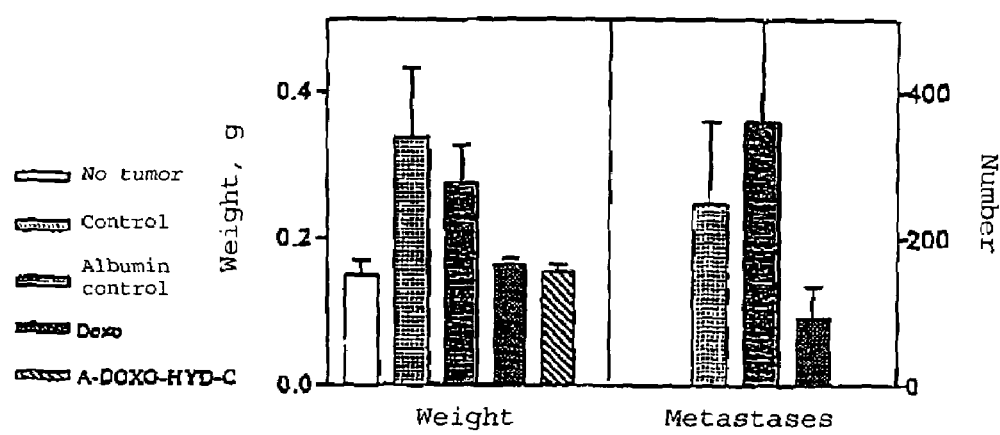

The results of this experiment are, further, graphically illustrated in FIG. 3 with respect to the weights and volumes of the kidneys and renal tumors (FIG. 3A) and the lung weights and the number of pulmonary metastases (FIG. 3B). A-DOXO-HYD-C shows a very good antitumoral effectiveness and brings about a complete remission in all animals. Macroscopically visible pulmonary metastases could be observed in only one animal (FIG. 3B). In the group treated with doxorubicin, plainly visible renal tumors were observed in all animals (FIG. 3A); that is, in contrast, no complete remissions were brought about at the optimal dose of doxorubicin (body weight loss −21% (d 1 to 25); 1 animal died). Furthermore, the number of pulmonary metastases was on average some 100 metastases per mouse in the mice treated with free doxorubicin (FIG. 3B).

SEQUENCE LISTING

```
<160> NUMBER OF SEQ ID NOS: 27

<210> SEQ ID NO 1
<211> LENGTH: 8
<212> TYPE: PRT
<213> ORGANISM: Artificial sequence
<220> FEATURE:
<223> OTHER INFORMATION: Octapeptide which stimulates the cleavage
      sequence of the collagen chain and is cleaved with particular
      efficiency by MMP2 and MMP9.

<400> SEQUENCE: 1

Gly Pro Leu Gly Ile Ala Gly Gln
1               5

<210> SEQ ID NO 2
<211> LENGTH: 8
<212> TYPE: PRT
<213> ORGANISM: Artificial sequence
```

```
<220> FEATURE:
<223> OTHER INFORMATION: Octapeptide which stimulates the cleavage
      sequence of the collagen chain and is cleaved with particular
      efficiency by MMP2 and MMP9.

<400> SEQUENCE: 2

Gly Pro Gln Gly Ile Trp Gly Gln
1               5

<210> SEQ ID NO 3
<211> LENGTH: 4
<212> TYPE: PRT
<213> ORGANISM: Artificial sequence
<220> FEATURE:
<223> OTHER INFORMATION: Peptide cleaved by cathepsin B

<400> SEQUENCE: 3

Gly Phe Leu Gly
1

<210> SEQ ID NO 4
<211> LENGTH: 4
<212> TYPE: PRT
<213> ORGANISM: Artificial sequence
<220> FEATURE:
<223> OTHER INFORMATION: Peptide cleaved by cathepsin B

<400> SEQUENCE: 4

Gly Phe Ala Leu
1

<210> SEQ ID NO 5
<211> LENGTH: 4
<212> TYPE: PRT
<213> ORGANISM: Artificial sequence
<220> FEATURE:
<223> OTHER INFORMATION: Peptide cleaved by cathepsin B

<400> SEQUENCE: 5

Ala Leu Ala Leu
1

<210> SEQ ID NO 6
<211> LENGTH: 16
<212> TYPE: PRT
<213> ORGANISM: Artificial sequence
<220> FEATURE:
<223> OTHER INFORMATION: Peptide containing two cleavage sites for MMP2
      and MMP9.

<400> SEQUENCE: 6

Gly Pro Leu Gly Ile Ala Gly Gln Gly Pro Leu Gly Ile Ala Gly Gln
1               5                   10                  15

<210> SEQ ID NO 7
<211> LENGTH: 12
<212> TYPE: PRT
<213> ORGANISM: Artificial sequence
<220> FEATURE:
<223> OTHER INFORMATION: Peptide containing several cleavage sites for
      cathepsin B.

<400> SEQUENCE: 7

Phe Lys Phe Lys Phe Lys Phe Lys Phe Lys Phe Lys
1               5                   10

<210> SEQ ID NO 8
```

```
<211> LENGTH: 6
<212> TYPE: PRT
<213> ORGANISM: Artificial sequence
<220> FEATURE:
<223> OTHER INFORMATION: Peptide containing several repetitive cleavage
      sites for cathepsin B.

<400> SEQUENCE: 8

Gly Gly Phe Lys Phe Lys
1               5

<210> SEQ ID NO 9
<211> LENGTH: 8
<212> TYPE: PRT
<213> ORGANISM: Artificial sequence
<220> FEATURE:
<223> OTHER INFORMATION: Octapeptide which is cleaved by MMP9.

<400> SEQUENCE: 9

Gln Gly Ala Ile Gly Leu Pro Gly
1               5

<210> SEQ ID NO 10
<211> LENGTH: 7
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 10

Gly Gly Gly Phe Lys Phe Lys
1               5

<210> SEQ ID NO 11
<211> LENGTH: 8
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 11

Gly Gly Gly Gly Phe Lys Phe Lys
1               5

<210> SEQ ID NO 12
<211> LENGTH: 9
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 12

Gly Gly Gly Gly Gly Phe Lys Phe Lys
1               5

<210> SEQ ID NO 13
<211> LENGTH: 10
<212> TYPE: PRT
<213> ORGANISM: Artificial
<220> FEATURE:
<223> OTHER INFORMATION: Peptide containing several repetitive cleavage
      sites for cathepsin B.
```

```
<400> SEQUENCE: 13

Gly Gly Gly Gly Gly Gly Phe Lys Phe Lys
1               5                   10

<210> SEQ ID NO 14
<211> LENGTH: 11
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 14

Gly Gly Gly Gly Gly Gly Gly Phe Lys Phe Lys
1               5                   10

<210> SEQ ID NO 15
<211> LENGTH: 12
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 15

Gly Gly Gly Gly Gly Gly Gly Gly Phe Lys Phe Lys
1               5                   10

<210> SEQ ID NO 16
<211> LENGTH: 13
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 16

Gly Gly Gly Gly Gly Gly Gly Gly Gly Phe Lys Phe Lys
1               5                   10

<210> SEQ ID NO 17
<211> LENGTH: 14
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 17

Gly Gly Gly Gly Gly Gly Gly Gly Gly Gly Phe Lys Phe Lys
1               5                   10

<210> SEQ ID NO 18
<211> LENGTH: 15
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 18

Gly Gly Gly Gly Gly Gly Gly Gly Gly Gly Gly Phe Lys Phe Lys
1               5                   10                  15
```

<210> SEQ ID NO 19
<211> LENGTH: 16
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 19

Gly Gly Gly Gly Gly Gly Gly Gly Gly Gly Gly Gly Phe Lys Phe Lys
1               5                   10                  15

<210> SEQ ID NO 20
<211> LENGTH: 17
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 20

Gly Gly Gly Gly Gly Gly Gly Gly Gly Gly Gly Gly Gly Phe Lys Phe
1               5                   10                  15

Lys

<210> SEQ ID NO 21
<211> LENGTH: 18
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 21

Gly Gly Gly Gly Gly Gly Gly Gly Gly Gly Gly Gly Gly Gly Phe Lys
1               5                   10                  15

Phe Lys

<210> SEQ ID NO 22
<211> LENGTH: 19
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 22

Gly Gly Gly Gly Gly Gly Gly Gly Gly Gly Gly Gly Gly Gly Gly Phe
1               5                   10                  15

Lys Phe Lys

<210> SEQ ID NO 23
<211> LENGTH: 20
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 23

Gly Gly Gly Gly Gly Gly Gly Gly Gly Gly Gly Gly Gly Gly Gly Gly
1               5                   10                  15

Phe Lys Phe Lys
        20

<210> SEQ ID NO 24
<211> LENGTH: 21
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 24

Gly Gly Gly Gly Gly Gly Gly Gly Gly Gly Gly Gly Gly Gly Gly
1               5                   10                  15

Gly Phe Lys Phe Lys
        20

<210> SEQ ID NO 25
<211> LENGTH: 22
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 25

Gly Gly Gly Gly Gly Gly Gly Gly Gly Gly Gly Gly Gly Gly Gly
1               5                   10                  15

Gly Gly Phe Lys Phe Lys
        20

<210> SEQ ID NO 26
<211> LENGTH: 23
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 26

Gly Gly Gly Gly Gly Gly Gly Gly Gly Gly Gly Gly Gly Gly Gly
1               5                   10                  15

Gly Gly Gly Phe Lys Phe Lys
        20

<210> SEQ ID NO 27
<211> LENGTH: 24
<212> TYPE: PRT
<213> ORGANISM: Artificial
<220> FEATURE:
<223> OTHER INFORMATION: Peptide containing several repetitive cleavage
      sites for cathepsin B.

<400> SEQUENCE: 27

Gly Gly Gly Gly Gly Gly Gly Gly Gly Gly Gly Gly Gly Gly Gly
1               5                   10                  15

Gly Gly Gly Gly Phe Lys Phe Lys
        20

The invention claimed is:

1. A medicament containing a carrier-drug conjugate and, optionally, a pharmaceutically compatible excipient, characterized in that
   (i) the carrier is native or recombinant albumin;
   (ii) the drug is a pharmaceutically and/or diagnostically active substance;
   (iii) the drug is bound to cysteine-34 of albumin over a spacer molecule and a thiol binding group;
   (iv) at least one of the spacer molecule, a linkage between spacer molecule and drug moiety and a linkage between spacer molecule and thiol binding group is cleavable hydrolytically and/or pH-dependently and/or enzymatically; and
   (v) at least 0.7 mol of said drug is bound to cysteine-34 per mol of albumin.

2. A medicament according to claim 1 wherein at least one of said spacer molecule and said linkage contains a peptide bond.

3. A medicament according to claim 2 which is cleavable by a protease.

4. A medicament according to claim 1 wherein at least one of said spacer molecule and said linkage is hydrolysable in an acidic medium.

5. A medicament according to claim 1 wherein said pharmaceutically active substance is selected from the group consisting of cytostatics, cytokines, immunosuppressants, antirheumatics, anti-inflammatories, antibiotics, analgesics, virostatics and antifungals.

6. A medicament according to claim 5 wherein the cytostatic pharmaceutically active substance is selected from the group consisting of
   anthracyclines, N-nitrosoureas, alkylating agents, purine or pyrimidine antagonists, folic acid antagonists, taxanes, camptothecins, podophyllotoxin derivatives, Vinca alkaloids, calicheamicins, maytansinoids and cis-configured platinum (II) complexes.

7. A medicament according to claim 1 wherein the diagnostically active substance contains at least one substance selected from the group consisting of radionuclides, one or a plurality of ligands containing radionuclides, positron emitters, NMR contrast media, fluorescing compound(s), and contrast media functional in the near IR region.

8. A medicament according to claim 1 in which the thiol binding group contains a maleinimide group, a haloacetamide group, a haloacetate group, a pyridyldithio group, a vinylcarbonyl group, an aziridine group, a disulfide group or an acetylene group, which groups may be substituted or unsubstituted.

9. A medicament according to claim 1 wherein said spacer molecule is selected from the group consisting of substituted or unsubstituted branched-chain or straight-chain aliphatic alkyl groups having 1 to 12 carbon atoms, substituted or unsubstituted aryl groups and aliphatic carbon rings having 3 to 12 carbon atoms.

10. A method for the preparation of carrier-drug conjugate contained in the medicament according to claim 1 comprising:
    (i) treating a carrier with a reducing agent so that at least 0.7 mol of cysteine SH groups is present in the carrier per mol of reducible cysteine groups; and
    (ii) coupling a drug to said cysteine SH groups in said carrier via the thiol-binding group.

11. A method according to claim 10 wherein said reducing agent is selected from the group consisting of dithiothreitol, dithioerythritol and mercaptoethanol.

12. A method according to claim 10 wherein said conjugate prepared exhibits a purity greater than 95%.

13. A medicament according to claim 1 for the treatment of cancer, autoimmune disorders, acute or chronically inflammatory diseases, or diseases that are caused by infectious agents selected from the group consisting of viruses and microorganisms.

14. A diagnostic kit comprising a medicament according to claim 1.

15. A diagnostic kit according to claim 14 for the detection of diseases selected from the group consisting of cancer, autoimmune disorders, acute or chronically inflammatory diseases, and diseases that are caused by infectious agents selected from the group consisting of viruses and microorganisms.

* * * * *